US006461873B1

(12) United States Patent
Catania et al.

(10) Patent No.: US 6,461,873 B1
(45) Date of Patent: Oct. 8, 2002

(54) CAFFEINE DETECTOR

(76) Inventors: Daniel Catania, 15280 Surry House Way, Centreville, VA (US) 20120; Steven Ignelzi, 1395 Oak Ct., Boulder, CO (US) 80304; Steven Baugh, 2931 N. Princess Cir., Broomfield, CO (US) 80020

( * ) Notice: Subject to any disclaimer, the term of this patent is extended or adjusted under 35 U.S.C. 154(b) by 0 days.

(21) Appl. No.: 09/528,194

(22) Filed: Mar. 17, 2000

Related U.S. Application Data
(60) Provisional application No. 60/124,934, filed on Mar. 18, 1999.

(51) Int. Cl.[7] ............................................. G01N 33/533
(52) U.S. Cl. ........................ 436/518; 436/20; 436/514; 436/525; 436/810; 436/816; 436/901; 435/7.1; 435/7.93; 435/970; 435/973; 435/975; 422/55; 422/56; 422/57; 422/58; 422/68.1; 422/102
(58) Field of Search ......................... 436/518, 20, 514, 436/525, 810, 816, 901; 422/55, 56, 57, 58, 68.1, 102; 435/7.1, 7.93, 7.94, 970, 287.2, 973, 288.4, 288.7, 975

(56) References Cited

U.S. PATENT DOCUMENTS

| | | | |
|---|---|---|---|
| 5,260,221 A | * | 11/1993 | Ramel et al. |
| 5,411,888 A | * | 5/1995 | Gordon et al. |
| 5,610,072 A | | 3/1997 | Scherl et al. |
| 5,814,223 A | | 9/1998 | Hjertén et al. |
| 5,817,454 A | | 10/1998 | Harris et al. |
| 5,821,311 A | | 10/1998 | Mosbach et al. |
| 5,824,554 A | | 10/1998 | McKay |
| 5,872,198 A | | 2/1999 | Mosbach et al. |
| 5,916,445 A | | 6/1999 | Hjertén et al. |
| 5,959,050 A | | 9/1999 | Mosbach et al. |
| 5,976,895 A | * | 11/1999 | Cipkowski |
| 6,268,210 B1 | * | 7/2001 | Baier et al. |

OTHER PUBLICATIONS

Lai, et al., Surface plasmon resonance sensors using molecularly imprinted polymers for sorbent assay of theophylline, caffeine, and xanthine, Can. J. Chem. vol. 76, pp. 265–273 (1998).

* cited by examiner

*Primary Examiner*—Bao-Thuy L. Nguyen
(74) *Attorney, Agent, or Firm*—Richard C. Litman

(57) ABSTRACT

The caffeine detector uses a paper chromatographic technique to measure the concentration of caffeine in a beverage. The device includes a well or other receptacle for containing a predetermined test volume of the beverage. A paper strip is suspended so that one end of the strip dips into the well. The strip is divided into two zones, the first zone being coated with at least one molecular imprint polymer (MIP) which absorbs substances which may interfere with quantification of caffeine. The second zone is coated with an MIP which selectively absorbs caffeine and chromogenic reagents which provide calorimetric visualization of the migration of caffeine through the second zone. The second zone bears indicia calibrating the paper strip so that the concentration of caffeine in the beverage may be determined by the height or distance which the caffeine migrates up the paper strip.

12 Claims, 2 Drawing Sheets

CAFFEINE DETECTOR

CROSS-REFERENCE TO RELATED APPLICATION

This application claims the benefit of U.S. Provisional Patent Application Serial No. 60/124,934, filed Mar. 18, 1999.

BACKGROUND OF THE INVENTION

1. Field of the Invnetion

The present invention relates generally to the detection of certain chemical substances. More specifically, the invention is a device for detecting the presence and concentration of caffeine in a beverage.

2. Description of Related Art

Many beverages contain caffeine as an active ingredient, such as coffee, tea, hot chocolate, and soft drinks. For many people caffeine serves as a useful stimulant. However, others may have an allergic reaction to caffeine. In addition, too much caffeine may result in insomnia, restlessness, and gastrointestinal problems. Pregnant or nursing women may wish to avoid caffeine for fear of harmful affects on their child. Caffeine also a diuretic effect on many individuals. For these reasons, it is often desirable to restrict the daily intake of caffeine or eliminate caffeine containing beverages from the diet.

Many of the known methods for identifying caffeine in a beverage and detecting the concentration of caffeine in the beverage are only suitable for use in the laboratory. It would therefore be desirable for the consumer to have a device for measuring the caffeine content of a beverage quickly and easily for use in the home, in restaurants, and the like. Such a device would enable the consumer to shun a beverage having a high caffeine concentration, or to reduce the quantity ingested to a safer level. A few devices have been proposed which are designed to permit the consumer to detect either the presence or the concentration of caffeine in a beverage, fluid, or other product.

U.S. Pat. No. 5,610,072, issued on Mar. 11, 1997 to Scherl, et al., discloses a dipstick and a method for detecting caffeine in beverages. The dipstick is impregnated with a reagent that changes color when reacted with caffeine. The dipstick preferably includes a beverage dipping section, an adjacent temperature moderation section, and an adjacent reagent-impregnated section. The device uses either enzymes or antibodies which react to produce hydrogen peroxide in the presence of caffeine, which subsequently reacts with a chromogen such as potassium iodide. The resulting color changes is compared with a color chart to determine the concentration of caffeine.

U.S. Pat. No. 5,817,454, issued on Oct. 6, 1998 to Harris, et al., discloses a portable apparatus and a method for detecting the presence of caffeine and the like in a beverage. The apparatus comprises a first portion comprising phosphodiesterase enzyme, a second portion comprising cyclic AMP, and a means for indicating inhibition of degradation of the cyclic AMP by the phosphodiesterase due to the presence of caffeine or the like. The method comprises contacting a portion of the beverage with a phosphodiesterase enzyme and cyclic AMP, and further contacting the portion with the means for indicating the inhibition, typically a pH indicator paper. The method produces a qualitative indication of the presence of caffeine, but not a quantitative measure of its concentration.

U.S. Pat. No. 5,824,554 issued on Oct. 20, 1998 to McKay discloses a method and a device for the detection of allergenic substances in food products. The device comprises a dining mat formed of an absorbent material with small spots of reagents applied to isolated zones on the mat. In use, the food product is applied to a reagent and if the food product contains the allergenic substance, the reagent will change its appearance. One of the allergenic substances tested for is caffeine, which produces a color change when reacted with Mayer's, Wagner's, or Dragendorff's reagents. The test is qualitative, and does not provide a quantitative measure of the amount of caffeine in the beverage or food product.

There are several problems with the above devices, at least to the extent that they are relied upon for quantitative information of the amount of caffeine in the beverage. The devices tend to be expensive to the extent that they rely upon enzymes or antibodies. The measurement of concentration by comparison of a color change to a chart can prove to be quite subjective. In terms of providing a quantitative measure of caffeine concentration, the devices appear not to require a measured volume of test sample, and thus are prone to error. Further, the devices provide no means for selectively absorbing caffeine from the test sample.

The caffeine detector of the present invention uses a molecular imprint polymer (MIP) as a chromatographic medium. A "molecular imprint polymer" is a polymer which is prepared by polymerizing monomers around a template or "print" molecule, which is then removed from the polymer by extraction or other means so that the polymer will selectively absorb the template or print molecule upon re-exposure to the print molecule. U.S. Pat. No. 5,821,311, U.S. Pat. No. 5,872,198, and U.S. Pat. No. 5,959,050, issued Oct. 13, 1998, Feb. 16, 1999, and Sep. 28, 1999, respectively, to Mosbach, et al. describe certain MIP polymers, a polymerization process, and symmetrical beads produced by suspension polymerization from functional monomers for use as chromatographic media. U.S. Pat. No. 5,814,223 and U.S. Pat. No. 5,916,445, issued Sep. 29, 1998 and Jun. 29, 1999, respectively, to Hjertén, et al., disclose a gel type chromatographic media and method for preparing the media, the media being formed by a molecular imprint polymer prepared from a nonionizable polymerizable substance which is nonreactive to the imprinted molecule.

An article by Lai, et al., in the Canadian Journal of Chemistry, Vol. 76, pp. 265–273 (1998) teaches the preparation of an MIP in which the template molecule is caffeine for the detection of small quantities of caffeine using an optical phenomenon known as surface plasma resonance. The polymer was prepared from methacrylic acid and ethylene glycol dimethacrylate in the presence of caffeine, which was subsequently removed by Soxhlet extraction. A thin overlayer of the polymer was placed on a silver film and showed selective absorption of caffeine as opposed to xanthine and theophylline, a similar methyl xanthine. Applicant obtained a sample of the MIP prepared by Dr. Lai. Although this polymer may be adequate for use in surface plasmon resonance, it proved unable to absorb sufficient caffeine for use as a caffeine detector, apparently due to too much cross-linking.

Consequently, the prior art fails to teach a device or practice which enables an operator to simply, safely, and reliably detect the concentration of caffeine in the beverage. None of the above inventions and patents, taken either singly or in combination, is seen to describe the instant invention as claimed.

SUMMARY OF THE INVENTION

The caffeine detector uses a paper chromatographic technique to measure the concentration of caffeine in a beverage.

The device includes a well or other receptacle for containing a predetermined test volume of the beverage. A paper strip is suspended so that one end of the strip dips into the well. The strip is divided into two zones, the first zone being coated with at least one molecular imprint polymer (MIP) which absorbs substances which may interfere with quantification of caffeine. The second zone is coated with an MIP which selectively absorbs caffeine and chromogenic reagents which provide calorimetric visualization of the migration of caffeine through the second zone. The second zone bears indicia calibrating the paper strip so that the concentration of caffeine in the beverage may be determined by the height or distance which the caffeine migrates up the paper strip.

Accordingly, it is a principal object of the invention to provide a simple, safe, and efficient device for detecting the presence or concentration of caffeine in a beverage.

It is another object of the invention to provide a simple, safe, and efficient device for detecting the presence or concentration of caffeine in the beverage which may be used by the ultimate beverage consumer on a per cup basis.

It is a further object of the invention to provide a device which utilizes a paper chromatographic method to determine the presence and concentration of caffeine.

It is an additional object of the invention to provide a device for measuring the presence and concentration of caffeine which uses a chromatographic medium having improved selectivity for caffeine.

It is an object of the invention to provide improved elements, arrangements, and steps thereof in a device and method for the purposes described above which are inexpensive, safe, efficient, and fully effective in accomplishing their intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
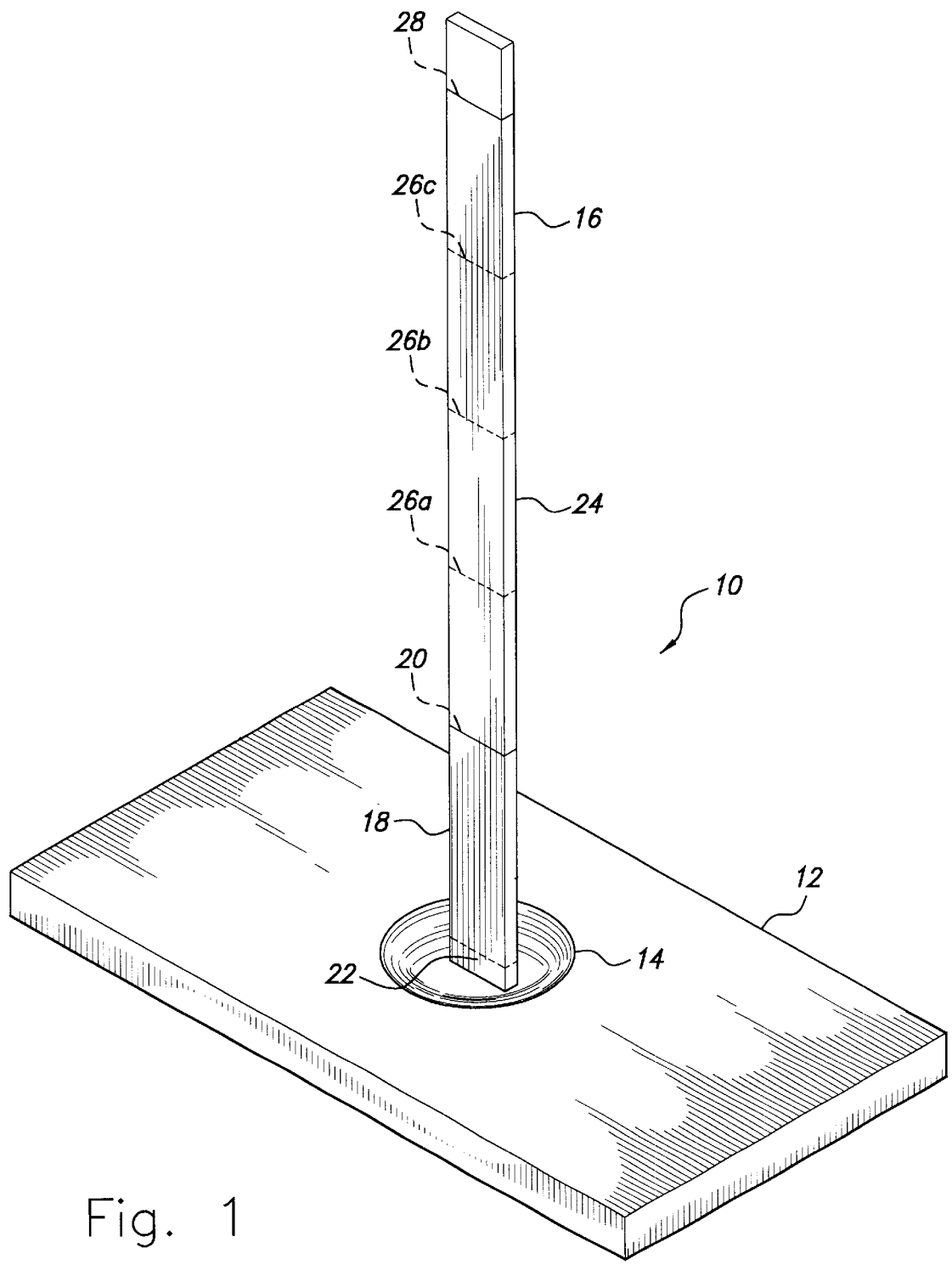
FIG. 1 is a perspective view of a caffeine detector according to the present invention, the support for the paper strip being omitted.

The caffeine detector of the present invention is a device which uses paper chromatographic methods to permit the ultimate consumer of a beverage to test the beverage for the presence and concentration of caffeine. The beverages tested may be coffee, tea, hot chocolate, soft drinks such as colas and Mountain Dew®, and other caffeine containing beverages. As shown in FIG. 1, the caffeine detector 10 has a base or platform 12 which has a well 14 defined therein. The well 14 is sized and dimensioned to contain a predetermined volume of a test sample of the beverage to bet tested. Preferably, the well 14 is calibrated to contain two milliliters (2 mL) of the beverage. The beverage may be transferred to the well 14 with an eye-dropper, spoon, or other means. The small volume of the well 14, shallow construction, and relatively broad surface area exposed to the air promotes rapid heating or cooling of the beverage to room temperature.

The caffeine detector 10 includes an elongated paper strip 16 which serves as a matrix or support for the stationary phase of chromatographic media. The paper is preferably conventional chromatography paper made from cellulose or other appropriate material. The paper strip 16 is divided into two zones. The first zone 18 extends from one end of the strip 16 to a point intermediate the opposing ends of the strip 16, designated by boundary line 20 extending horizontally across the strip 16 in FIG. 1. The paper strip 16 is suspended above the base 12 so that a portion 22 of the first zone 18 dips into the well 14 and any test sample in the well 14 is drawn up the strip 16 by capillary action. The first zone 18 is characterized in that it may be coated, impregnated, embedded, treated, or otherwise supporting a chromatographic media which includes at least one molecular imprint polymer (MIP) which selectively retains compounds, such as theobromine and other related organic amine compounds, commonly found in the beverage which may interfere with detection of the presence and concentration of caffeine.

The MIP used as the stationary phase in the first zone 18 may be synthesized as follows. The reactants shown in Table I are added to 35 mL of chloroform.

The mixture is sonicated for about fifteen seconds and degassed in a rotary evaporator under pressure. The mixture is then purged with nitrogen gas for fifteen minutes at room temperature and then kept under low nitrogen flow at 60° C. in a circulating water bath for twenty four hours. Additional chloroform is added every two to three hours through a reflux condenser to maintain a layer of solvent above the developing polymer. The polymer produced is a white solid which is ground to a particle size less than 180 μm, and preferably less than 38 μm in order to provide particles having a greater surface area. The imprint molecule (theobromine) is then extracted from the polymer. The polymer may be extracted by serial extractions with chloroform, including forty-five minutes sonication, centrifuging, and decanting the solvent layer. The samples are then dried overnight. Better removal of the imprint molecule should be attainable by Soxhlet extraction for about twenty-four hours.

The second zone 24 extends from the terminating boundary 20 of the first zone 18 to the opposing end of the strip 16. The stationary phase in the second zone 24 includes a molecular imprint polymer (MIP) which selectively absorbs caffeine. As the test sample migrates up the paper strip 16 by capillary action, any caffeine is absorbed by the MIP. However, the absorption capacity of the MIP is finite. Consequently, as the templates or imprints in the MIP become filled with caffeine molecules, the caffeine migrates higher. Absorption of caffeine by the MIP retards the migration of caffeine up the paper strip 24.

The MIP for the stationary phase of the second zone 24 may be synthesized as follows. The reactants shown in Table II are added to 35 mL of chloroform.

TABLE II

| | |
|---|---|
| Methacrylic acid | 1.0 g. |
| Ethylene glycol dimethacrylate | 5.0 g. |
| 2,2'-azobis(2-methylproprionitrile) | 0.12 g. |
| Toluene | 0.56 g. |
| Caffeine | 2.0 g. |

The mixture is sonicated for about fifteen seconds and degassed in a rotary evaporator under pressure. The mixture is then purged with nitrogen gas for fifteen minutes at room temperature and then kept under low nitrogen flow at 60° C. in a circulating water bath for twenty four hours. Additional chloroform is added every two to three hours through a reflux condenser to maintain a layer of solvent above the developing polymer. The polymer produced is a white solid which is ground to a particle size less than 180 μm, and preferably less than 38 μm in order to provide particles having a greater surface area. The imprint molecule (caffeine) is then extracted from the polymer. The polymer may be extracted by serial extractions with chloroform, including forty-five minutes sonication, centrifuging, and decanting the solvent layer. The samples are then dried overnight. Better removal of the imprint molecule should be attainable by Soxhlet extraction for about twenty-four hours.

The foregoing synthesis procedure is similar to the procedure outlined by Lai, et al., supra. However, the polymer provided by Lai, et al., proved to have insufficient caffeine absorption capacity for use as a caffeine detector in the present application. The polymer produced by the synthesis procedure outlined by Lai, et al., is characterized by extensive cross-linking to provide greater strength for surface plasmon resonance spectroscopy techniques, which requires a material able to withstand high pressure. The procedure outlined by Lai, et al., was designed for analysis of trace amounts of organic material, consequently a large absorption, capacity was not required. The synthesis procedure of the present invention produces greater absorption capacity for caffeine by reducing the amount of cross-linker (ethylene glycol dimethacrylate) and increasing the amount of imprint molecule. In addition, the synthesis procedure of the present invention adds toluene as a "porogen", i.e., terminating polymerization and creating "pores" within the bulk of the material. This allows liquid to travel within the bulk of the particle, increasing surface area for adsorption with the same particle size. The synthesis procedure according to the present invention also permits easier grinding of the particles, enabling a smaller particle size (less than 38 μm) to be achieved. The result is a polymer with a greater weight/weight absorption capacity for caffeine, making quantitative paper chromatography feasible. The above synthesis procedure resulted in a 2.12% weight/weight absorption capacity, as shown by high performance liquid chromatography.

Since caffeine ordinarily cannot be visualized on the paper strip 16, the stationary phase in the second zone 24 also includes chromogenic reagents which react with the caffeine absorbed by the MIP to produce a colored compound which may be visualized in contrast to the paper strip 16. Such chromogenic reagents may include peroxides and oxidizers which react with caffeine to produce a color reaction. Suitable chromogenic reagents include Mayer's reagent, Wagner's reagent, or Dragendorff's reagent. Alternatively, various enzymes including oxidase and peroxidase enzymes, or monoclonal antibodies may be used for producing a chromogenic reaction, as is known in the art.

The second zone 24 is calibrated and contains a plurality of indicia, such as horizontal lines 26, which correspond to the number of milligrams of caffeine present in, e.g., an eight ounce cup of the beverage. Although the paper strip 16 could be calibrated to reflect the number of milligrams contained in the 2 mL test sample, this would require that the consumer perform a number of calculations to convert units, etc. By calibrating the, paper strip 16 in milligrams per standard serving, the consumer may read the caffeine content directly from the paper strip 16. Although the indicia is shown in the drawings as horizontal lines 26, it will be obvious that the indicia may include numerical figures corresponding to the number of milligrams at each horizontal line 26.

The caffeine concentration is determined solely by the height or distance the caffeine migrates along the paper strip 16. The chromogenic reagents are used simply to visualize the extent of travel of the caffeine. The horizontal lines 26 may be placed at any convenient concentration level, e.g., the lowest line 26a may represent up to thirty milligrams of caffeine per eight ounces of beverage, the second line 26b may represent up to 60 milligrams per eight ounces of beverage, the third line 26c may represent up to ninety milligrams per eight ounces of beverage, etc. In use, the consumer will wait until the solvent, or test sample, rises to the top of the paper strip 16 before reading the concentration. The paper strip 16 may have a test termination line 28 adjacent the end of the second zone 24 to signify to the consumer that the concentration should be read when the leading edge of the test sample rises to the test termination line 28.

Figure 2:
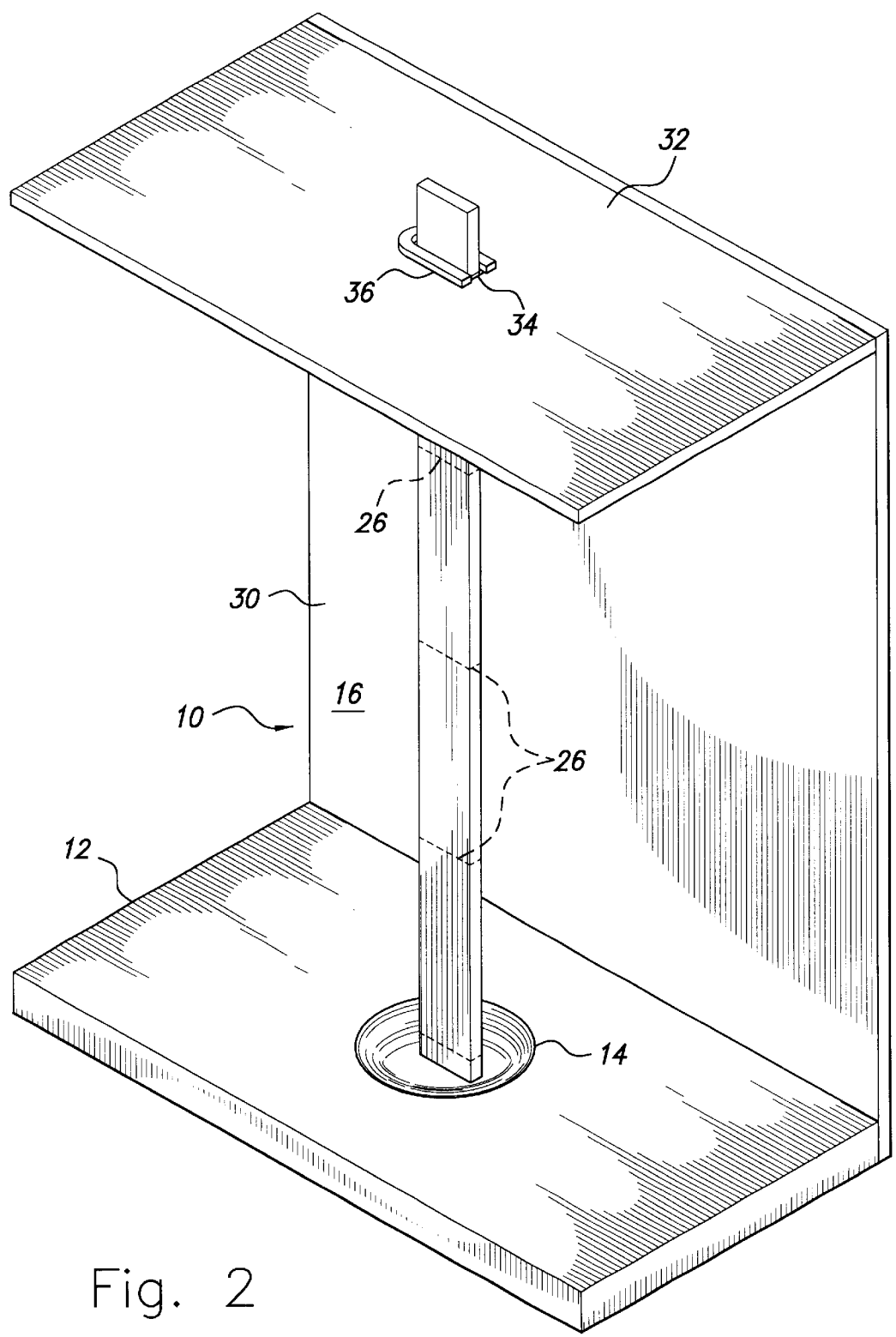
FIG. 2 is a perspective view of a caffeine detector according to the present invention.

The paper strip 16 may be supported above the well 14 in any convenient manner. As shown in FIG. 2, the caffeine detector 10 may further comprise a vertical wall 30 attached to an edge of the base 12, and a strip support wall 32 extending parallel to the base 12 above the well 14. The wall 32 may have a slot 34 defined therein through which a paper strip 16 may be inserted and retained at an appropriate height by a clip 36, such as a paper clip. It will be understood that the description of the particular support structure shown in FIG. 2 is for purposes of illustrating an example of how the invention may be carried out, and that other methods of packaging and supporting the chromatographic paper strip 16 are intended to be comprehended within the present invention, the only requisites for the present invention being a well 14, container or other chamber for containing a predetermined test volume of the beverage, a paper strip 16 as described above, and any convenient means for supporting the paper strip 16 so that it may be suspended above the test sample with a portion of the first zone 18 submerged in the test sample.

It will be obvious to those skilled in the art that the principles of the present invention, and particularly to the chromatographic media described herein, may be applied to preparation of a slide for thin layer chromatography, for a media which may be disposed in a packed column for elution chromatography, or to a gel medium disposed in a column. It is to be understood that the present invention is not limited to the sole embodiments described above, but encompasses any and all embodiments within the scope of the following claims.

We claim:

1. A caffeine detector for detecting the presence and concentration of caffeine in a liquid, the detector comprising an elongated strip of absorbent paper having:

a) a first zone having a stationary phase disposed thereon including a first molecular imprint polymer for selectively absorbing compounds interfering with the detection of caffeine; and b) a second zone having a stationary phase disposed thereon including a second molecular imprint polymer for selectively absorbing caffeine and at least one chromogenic agent which produces a color change in the presence of caffeine; and c) said paper strip being suspended above a predetermined volume of a liquid with a portion of the first zone dipping into the liquid, the presence and concentration of caffeine in the liquid is determined by the height of the color change produced in the second zone.

2. The caffeine detector according to claim 1, further comprising a plurality of indicia imprinted on said paper strip in the second zone calibrated to correspond to the caffeine concentration in a predetermined volume of a liquid being analyzed.

3. The caffeine detector according to claim 1, wherein said first molecular imprint polymer consists essentially of a polymer polymerized from methacrylic acid cross-linked with ethylene glycol dimethacrylate in the presence of theobromine and a porogen, said polymer having a capacity for selectively absorbing theobromine.

4. The caffeine detector according to claim 3, wherein said first molecular imprint polymer has a particle size less than one hundred eighty micrometers.

5. The caffeine detector according to claim 3, wherein said first molecular imprint polymer has a particle size less than thirty-eight micrometers.

6. The caffeine detector according to claim 1, wherein said second molecular imprint polymer consists essentially of a polymer polymerized from methacrylic acid cross-linked with ethylene glycol dimethacrylate in the presence of caffeine and a porogen, said polymer having a capacity for selectively absorbing caffeine.

7. The caffeine detector according to claim 6, wherein said second molecular imprint polymer has a particle size less than one hundred eighty micrometers.

8. The caffeine detector according to claim 6, wherein said second molecular imprint polymer has a particle size less than thirty-eight micrometers.

9. The caffeine detector according to claim 1, further comprising a base platform having a well defined therein, said paper strip being suspended above said base platform with a portion of the first zone dipping into the well.

10. The caffeine detector according to claim 9, wherein said well is calibrated to contain a predetermined volume of a liquid for analysis.

11. The caffeine detector according to claim 9, wherein said well is calibrated to contain about two milliliters of a liquid for analysis.

12. The caffeine detector according to claim 9, further comprising:
 a) a vertical wall attached to said base platform; and
 b) a support wall attached to said vertical wall and extending parallel to and above said base platform, the support wall having a slot defined therein aligned above said well, said paper strip being inserted through said slot with a portion of the first zone dipping into said well.

* * * * *